(12) United States Patent
Taffler

(10) Patent No.: US 12,059,308 B2
(45) Date of Patent: *Aug. 13, 2024

(54) MODULAR ULTRASONIC TRANSDUCERS AND FRAME

(71) Applicant: ACOUSTIIC INC., Pacific Palisades, CA (US)

(72) Inventor: Sean Taffler, Pacific Palisades, CA (US)

(73) Assignee: Acoustic Inc., Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/963,557

(22) Filed: Oct. 11, 2022

(65) Prior Publication Data

US 2023/0124320 A1 Apr. 20, 2023

Related U.S. Application Data

(63) Continuation of application No. 17/066,180, filed on Oct. 8, 2020, now Pat. No. 11,464,497.

(60) Provisional application No. 62/913,067, filed on Oct. 9, 2019.

(51) Int. Cl.
*A61B 8/00* (2006.01)
(52) U.S. Cl.
CPC ............ *A61B 8/546* (2013.01); *A61B 8/4209* (2013.01); *A61B 8/4411* (2013.01); *A61B 8/4488* (2013.01)
(58) Field of Classification Search
CPC ..... A61B 8/546; A61B 8/4209; A61B 8/4411; A61B 8/4488; A61B 8/565; B06B 1/02
See application file for complete search history.

(56) References Cited

U.S. PATENT DOCUMENTS

| | | |
|---|---|---|
| 2012/0095347 A1 | 4/2012 | Adam |
| 2013/0158385 A1 | 6/2013 | Barnes |
| 2014/0316269 A1 | 10/2014 | Zhang |
| 2015/0345987 A1 | 12/2015 | Hajati |
| 2016/0120059 A1* | 4/2016 | Shedd ............... F28D 21/00 165/244 |
| 2017/0360413 A1* | 12/2017 | Rothberg ............ G01S 15/8952 |
| 2018/0125461 A1* | 5/2018 | Clark ................... A61B 8/4444 |
| 2019/0021666 A1* | 1/2019 | Hynynen ............... A61B 90/14 |

(Continued)

OTHER PUBLICATIONS

International Search Report and Written Opinion for App. No. PCT/US2020/055029, dated Feb. 5, 2021, 12 pages.

(Continued)

*Primary Examiner* — Alexei Bykhovski
(74) *Attorney, Agent, or Firm* — Ian Harrison; BUTZEL LONG

(57) ABSTRACT

Apparatuses, systems, and techniques are provided for modular ultrasonic transducers and frame. An ultrasonic transducer array may include a modular ultrasonic transducer array frame. The modular ultrasonic transducer array frame may include mechanisms for the attachment of ultrasonic transducer modules to the ultrasonic transducer array frame. The ultrasonic transducer array may include ultrasonic transducer modules which may include arrays of ultrasonic transducer elements within the ultrasonic transducer modules. Two of the ultrasonic transducer modules may include arrays of ultrasonic transducer elements where the ultrasonic transducer elements are different between the two ultrasonic transducer modules.

18 Claims, 7 Drawing Sheets

(56) References Cited

U.S. PATENT DOCUMENTS

2019/0143149 A1* 5/2019 Sverdlik ............... B06B 1/0662
  601/2
2019/0200959 A1* 7/2019 Chaggares ........... A61B 8/4488
2019/0262634 A1* 8/2019 Barthe .................... A61B 8/08
2021/0069749 A1   3/2021 Durocher

OTHER PUBLICATIONS

International Preliminary Report on Patentability issued in App. No. PCT/US2020/055029, dated Apr. 21, 2022, 3 pages.

* cited by examiner

MODULAR ULTRASONIC TRANSDUCERS AND FRAME

BACKGROUND

Ultrasonic transducers may have a number of different uses, and different types of ultrasonic transducers may be more suitable for use in different situations. Some situations may benefit from a mix of types of ultrasonic transducers. Creating an array of ultrasonic transducers may be difficult when the array uses a mix of different types of ultrasonic transducers.

BRIEF SUMMARY

According to an implementation of the disclosed subject matter, a modular ultrasonic transducer array frame may include mechanisms for the attachment of ultrasonic transducer modules to the ultrasonic transducer array frame. The ultrasonic transducer array may include ultrasonic transducer modules which may include arrays of ultrasonic transducer elements within the ultrasonic transducer modules. Two of or more of the ultrasonic transducer modules may include arrays of ultrasonic transducer elements where the ultrasonic transducer elements are different between the two or more ultrasonic transducer modules.

Additional features, advantages, and implementations of the disclosed subject matter may be set forth or apparent from consideration of the following detailed description, drawings, and claims. Moreover, it is to be understood that both the foregoing summary and the following detailed description provide examples of implementations and are intended to provide further explanation without limiting the scope of the claims.

FIG. 1 shows an example ultrasonic transducer array according to an implementation of the disclosed subject matter.

FIG. 2 shows an example ultrasonic transducer array according to an implementation of the disclosed subject matter.

FIG. 3 shows example ultrasonic transducer modules according to an implementation of the disclosed subject matter.

FIG. 4 shows an example ultrasonic transducer array frame according to an implementation of the disclosed subject matter.

FIG. 5 shows an example ultrasonic transducer module according to an implementation of the disclosed subject matter.

FIG. 6 shows an example ultrasonic transducer array and cooling fluid chamber according to an implementation of the disclosed subject matter.

FIG. 7 shows a computer according to an embodiment of the disclosed subject matter.

FIG. 8 shows a network configuration according to an embodiment of the disclosed subject matter.

BRIEF DESCRIPTION OF THE DRAWINGS

The accompanying drawings, which are included to provide a further understanding of the disclosed subject matter, are incorporated in and constitute a part of this specification. The drawings also illustrate implementations of the disclosed subject matter and together with the detailed description serve to explain the principles of implementations of the disclosed subject matter. No attempt is made to show structural details in more detail than may be necessary for a fundamental understanding of the disclosed subject matter and various ways in which it may be practiced.

DETAILED DESCRIPTION

Figure 1:
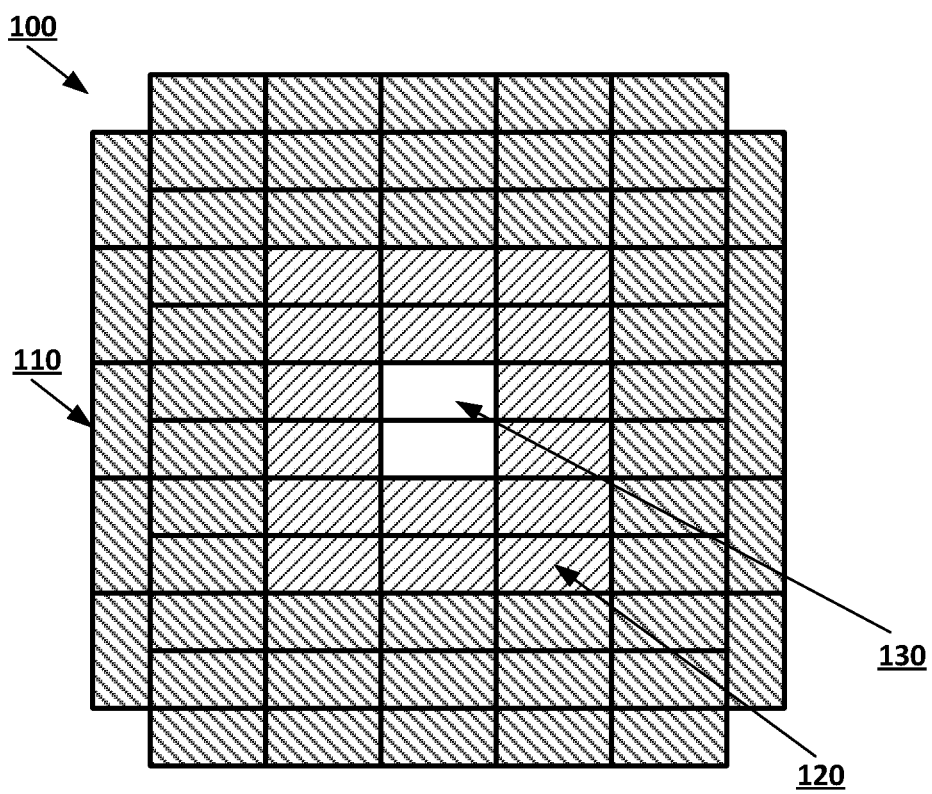

Ultrasonic transducers of varying types may be built with a common interface to the drive and receive electronics of the ultrasonic transducers to create ultrasonic transducer modules. There may be a number of different types of ultrasonic transducers, such as, for example lead zirconate titanate (PZT) transducers, piezoelectric micromachined ultrasonic transducers (PMUTs), capacitive micromachined ultrasonic transducers (CMUTs), and single crystal transducers. Each type of ultrasonic transducer may have drive and/or receive electronics that may be different from the drive and/or receive electronics of other types of ultrasonic transducers. The different types of ultrasonic transducers may be built into an ultrasonic transducer module with a single type of electronics interface. This electronics interface may be a common interface among ultrasonic transducer modules that each include different types of ultrasonic transducer elements. This may allow a mix of different types of ultrasonic transducers to be used in ultrasonic transducer arrays of varying sizes and orientations. Some ultrasonic transducer may have only drive electronics, and some ultrasonic transducers may have only receive electronics.

The common interface may provide an electrical or optical connection through which electrical or optical signals may be provided to the drive and receive electronics that control the operation of ultrasonic transducers in the ultrasonic transducer module from an outside source in order to control, operate and power the ultrasonic transducer, and through which electrical or optical signals may be carried out of the ultrasonic transducer module from the drive and receive electronics. The common interface may allow electrical connections to be daisy chained between ultrasonic transducer modules, or the common interface may allow for an electrical connection between ultrasonic transducer modules and a common backplane, which may be rigid or flexible. The common interface may also allow for the cooling fluids to be distributed to the ultrasonic transducer modules through a daisy chain, or for the ultrasonic transducer modules to be directly connected to a remote manifold. The common interface may, for example, include a first and second connection points at different locations on an ultrasonic module. The first and second connection points may be, for example, intake and exit ports which may also allow the circulation of fluids through daisy chained ultrasonic transducer modules. The first and second connection points may be located at any suitable location an ultrasonic transducer module. For example, a first connection point may be located on one side of an ultrasonic transducer module while the second connection point may be located on a different side, such as the opposite side. An ultrasonic transducer module may optionally include additional connection points which may provide flexibility when connecting ultrasonic transducer modules together to form a daisy chain. Connection points may allow an ultrasonic transducer module to be connected to another ultrasonic transducer module that uses the common interface and include connection points. The connection points may allow for a physical coupling of ultrasonic transducer modules, for example, attaching ultrasonic transducer modules to each other mechanically while allowing for the passing of electrical or optical signals and the circulation of fluids between ultrasonic transducer modules, or may be contact-based connection points that allow for the passing of electrical or optical signals between ultrasonic transducer modules but do not physically attach the ultrasonic transducer modules to each other. Thermal shunts may be provided between the ultrasonic modules, which may allow ultrasonic transducer modules to be packed close together, creating a higher density of ultrasonic transducer modules, while allowing removal of heat from the ends and sides.

The ultrasonic transducer modules may be of any suitable size and shape. Different ultrasonic transducers may be used to create ultrasonic transducer modules of the same size and shape, or the size and shape of an ultrasonic transducer module may be different depending on the type of ultrasonic transducer used in the ultrasonic transducer module. An ultrasonic transducer module may include any number of individual ultrasonic transducer elements. For example, a single ultrasonic transducer module may be an array of ultrasonic transducers of a particular type, and different ultrasonic transducer modules may use different types of ultrasonic transducer elements. A housing of an ultrasonic transducer module may be made of any suitable material, and may have connection points implemented in any suitable manner, including through the shape of the housing, the addition of mechanical components to the housing, or vias in the surface of the housing that allow for electrical or optical connections to be passed from the outside of the housing to the inside of the housing.

The ultrasonic transducer modules may be assembled into a frame that may define the physical position of the ultrasonic transducer modules in space to create an ultrasonic transducer array. The frame may be customized based on the intended use of the ultrasonic transducer array, allowing for ultrasonic transducer arrays of various sizes, three-dimensional shapes, and orientations. The ultrasonic transducers may, for example, have square, hexagonal, or rectangular profiles, or profiles of any suitable shape, and may have any suitable three-dimensional shape. The ultrasonic transducers of the ultrasonic transducer modules may be optimized for different frequency output, steering/directivity, and/or power output. Ultrasonic transducers with different ultrasonic transducer types may be mixed in the same frame, creating a blended ultrasonic transducer array that may be optimized for a particular function or use. For example, an ultrasonic transducer array may be optimized for shear wave imaging or ablative therapy with integrated imaging for guidance and therapy progression tracking.

Ultrasonic transducer modules and frames may be used to create large ultrasonic transducer arrays that may be invariant in resolution against depth. For example, a frame may include a small array of ultrasonic transducer modules with high frequency transducers surrounded by an array of ultrasonic transducer modules with lower frequency transducers for achieving penetration, and which may be surrounded in turn by a larger array of ultrasonic transducer modules with lower frequency transducers to allow the ultrasonic transducer array to achieve an appropriate maximum penetration depth. The ultrasonic transducer modules in the ultrasonic transducer array may be of different sizes and shapes, and may be arranged in any suitable patterns. For example, ultrasonic transducer modules may be arranged in concentric rings, which each ring including ultrasonic transducer modules with ultrasonic transducers of a specific type, or may be arranged in halves, quadrants, checkerboard patterns, or any other suitable pattern. Increasing the active area of the ultrasonic transducer array while maintaining all other parameter may improve the resolution of the ultrasonic transducer array. The number of ultrasonic transducer modules with ultrasonic transducers for each frequency array may increase to maintain the effective spatial resolution at target depth. Individual ultrasonic transducer modules may include more than one ultrasonic transducer.

The frame may include any suitable mechanism for the connection or attachment of ultrasonic transducer modules to the frame. For example, the frame may include slots into which the ultrasonic transducer modules may be inserted and held in place, for example, through friction fitting or through other mechanisms. The ultrasonic transducer modules may be attached to the frame through mechanical connections formed by parts of the frame and parts of the housings of the ultrasonic transducer modules. In some implementations, the frame may include a backplane to which the ultrasonic transducer modules may be attached and to which the common interface of the ultrasonic transducer modules may be connected, allowing for drive and receive signals to be transmitted to the ultrasonic transducer elements of the ultrasonic transducer modules.

A software component of an ultrasonic controller system may be used with an ultrasonic transducer array to allow an ultrasonic controller system to know the position of the ultrasonic transducer modules, and individual ultrasonic transducers, in time and space. For example, the ultrasonic controller system may run on any suitable computing device that may be part of, or connected to the ultrasonic transducer array and may control the operation of the ultrasonic transducers in the ultrasonic transducer modules. The ultrasonic controller system may use a general-purpose processor or may use a special processor or other electronics.

The location of an ultrasonic transducer module in space may be given by a six degrees of freedom vector, [x,y,z], plus rotations relative to a common reference frame. The electrical propagation delay for the signal paths for the ultrasonic transducer array may be calculated based on the electrical propagation of signals in wires and the architecture of the ultrasonic transducer array. For any two components, one of which is an ultrasonic receiver at position [0,0,0] and the second of which is a transmitting ultrasonic transducer module at position [X,Y,Z], the electrical propagation delays to each of these components may be calculated based on the electro mechanical design of the ultrasonic transducer array. Knowing the rotation of the ultrasonic transducer module may allow for transmit beam and receive directional cone to be located in space. A pulse transmitted from the transmitting ultrasonic transducer module and received by the receiver will have a propagation delay of: Time-of-Electrical-propagation-computer-to-transmitter+Time-of-acoustic-propagation-through-medium+Time-of-propagation-receiver-to-computer. The distance between the transmitting ultrasonic transducer and ultrasonic receiver may be calculated based on the speed of propagation of sound through the medium. If a second ultrasonic receiver is used at a different position the position of the transmitting ultrasonic transducer module can be further resolved. Two transmitting ultrasonic transducer modules and multiple ultrasonic receivers may be used to more efficiently calculate the positions of the ultrasonic receivers.

The time component of the location of an ultrasonic transducer module may be based on the propagation delay for electrical signals in reaching the ultrasonic transducer of an ultrasonic transducer module and the acoustic propagation delay associated with each ultrasonic transducer. Given a fixed reference frame within the ultrasonic transducer array, the ultrasonic transducer modules may be dynamically manipulated to alter their positions. The ultrasonic transducer modules may be repositioned electrically, electromechanically, hydraulically, or mechanically.

Ultrasonic transducer modules may be mechanically displaced when generating pulses of high energy ultrasonic waves, as used in some imaging and therapy modalities, such as acoustic radiation force imaging (ARFI) or high-intensity focused ultrasound (HIFU). The frame for the ultrasonic transducer array may be a smart frame that may have embedded sensors, such as strain gauges, which may allow for measurement of and compensation for unintended movement of the ultrasonic transducer modules. The absolute displacement of ultrasonic transducer modules relative to a target surface may also be measured using, for example, laser interferometers or linear variable differential transformer (LVDT) sensors. Displacement may also be determined without sensors, for example, by using an analytical model that may describe the displacement of ultrasonic transducer modules within the frame for a given pulse of high energy ultrasound, or by using a look up table that may correlate pulses of high energy ultrasound, for example, by energy level, with the displacement they cause in ultrasonic transducer modules.

The ultrasonic transducer modules and the frame may include identifiable fiducials. The fiducials may allow the positions of the ultrasonic transducer modules to be accurately registered in other imaging modalities, such as magnetic resonance imaging (MRI) or computed tomography (CT). Fiducials may be positioned on any suitable surface of a frame or an ultrasonic transducer module, including outer and inner surfaces. The fiducials may also be used to code unique properties or identifiers for each ultrasonic transducer module of the ultrasonic transducer array. Ultrasonic transducer modules of different shapes may use differently shaped fiducials or may be encoded with a transducer type pattern. The fiducial shape or pattern may be resolvable by various imaging modalities, such as magnetic resonance (MR) or CT. One fiducial can be placed on an ultrasonic transducer module to indicate the location of the Zero Element of ultrasonic transducer module. The Zero Element may be, for example, an ultrasonic transducer element that is considered to be located at the position [0,0] on the array of the ultrasonic transducers in the ultrasonic transducer module. Some ultrasonic transducer module shapes may allow for multiple orientations. Knowledge of one fiducial of an ultrasonic transducer module and of the transducer type may allow for determination of the orientation of the ultrasonic transducer module. Second and third fiducials on the ultrasonic transducer module may allow for confirmation of the orientation of the ultrasonic transducer module, increase the accuracy of the determination of the location and orientation of the ultrasonic transducer module, and provide redundancy for failed fiducials. A pattern may be placed into a fiducial that may be resolvable by imaging a one-dimensional line pattern, such as a bar code, or a two-dimensional pattern, such as a QR code. The pattern may provide additional information about the ultrasonic transducer module, such as, for example, a part number. An ultrasonic transducer module may also include an embedded RFID tag that may provide additional information about the ultrasonic transducer.

Fiducials may also be placed on a frame. For example, a fiducial on a frame may mark the location of the ultrasonic transducer module that serves as the zero module. The zero module may be the ultrasonic transducer module that is considered to be located at [0,0] in the array of ultrasonic transducer modules. Additional fiducials may be added to a frame to allow for more accurate determination of the orientation of the frame. If the frame is flexible, additional fiducials may be added to the movable sections of the frame so that shape of the frame may be determined based on the locations of the fiducials. The fiducials on the frame may be in addition to fiducials on the ultrasonic transducer modules, which may also be used to determine the shape of a flexible frame.

In some implementations, a cooling fluid chamber may be used in front of or surrounding the front portion of the ultrasonic transducer array. The cooling fluid may be, for example, water. The cooling fluid chamber may have a membrane across its front that may be in contact with the target of the ultrasonic waves and may pass ultrasonic energy to the target. The membrane may be coated, for example, with planar graphite or diamond-like carbon (DLC), or any other suitable highly thermally conductive material which may allow for dispersal of surface hot spots. The coating may also act as an RF shield, which may improve the signal-to-noise ratio (SNR) of the ultrasonic transducer array by keeping out unwanted RF energy and/or preventing emissions of RF energy from the ultrasonic transducer array. The frame of the ultrasonic transducer array may also be coated with a material similar to the material used to coat the membrane, allowing for similar reductions in RF interference. The depth of the cooling fluid chamber may be adjustable, allowing for the gap between the target and front of the ultrasonic transducer array to be tuned, which may disguise gaps between the ultrasonic transducer modules. This may allow better imaging with the ultrasonic transducer array that uses ultrasonic transducer modules while also allowing the ultrasonic transducer array to be positioned close to the surface target in situations where close coupling is desired. In some implementations, cooling fluid may be circulated through the ultrasonic transducer array in order to cool the ultrasonic transducer elements and electronics.

The use of ultrasonic transducer modules may allow for techniques from adaptive optics to be used with ultrasonic transducer arrays, including ultrasonic transducer array that may be part of imaging and therapy systems.

FIG. 1 shows an example ultrasonic transducer array according to an implementation of the disclosed subject matter. An ultrasonic transducer array 100 may include different ultrasonic transducer types in the form of ultrasonic transducer modules, assembled into a frame. The ultrasonic transducer modules 110 may include low frequency ultrasonic transducers. Each of the ultrasonic transducer modules 110 may include an array of any suitable size and shape of ultrasonic transducer elements designed to operate at low frequencies. The ultrasonic transducer modules 120 may include medium frequency ultrasonic transducers. Each of the ultrasonic transducer modules 120 may include an array of any suitable size and shape of ultrasonic transducer elements designed to operate at medium frequencies. The ultrasonic transducer modules 130 may include high frequency ultrasonic transducers. Each of the ultrasonic transducer modules 130 may include an array of any suitable size and shape of ultrasonic transducer elements designed to operate at high frequencies.

The ultrasonic transducer array 100 may be constructed using a frame. The frame may accommodate the ultrasonic transducer modules, such as the ultrasonic transducer modules 110, 120, and 130. The frame may, for example, include a number of slots into which the ultrasonic transducer modules 110, 120, and 130 may be inserted, or may include any other suitable mechanism for allowing the ultrasonic transducer modules 110, 120, and 130 to be connected or otherwise attached to the frame and held in position during operation of ultrasonic transducer array 100.

Figure 2:
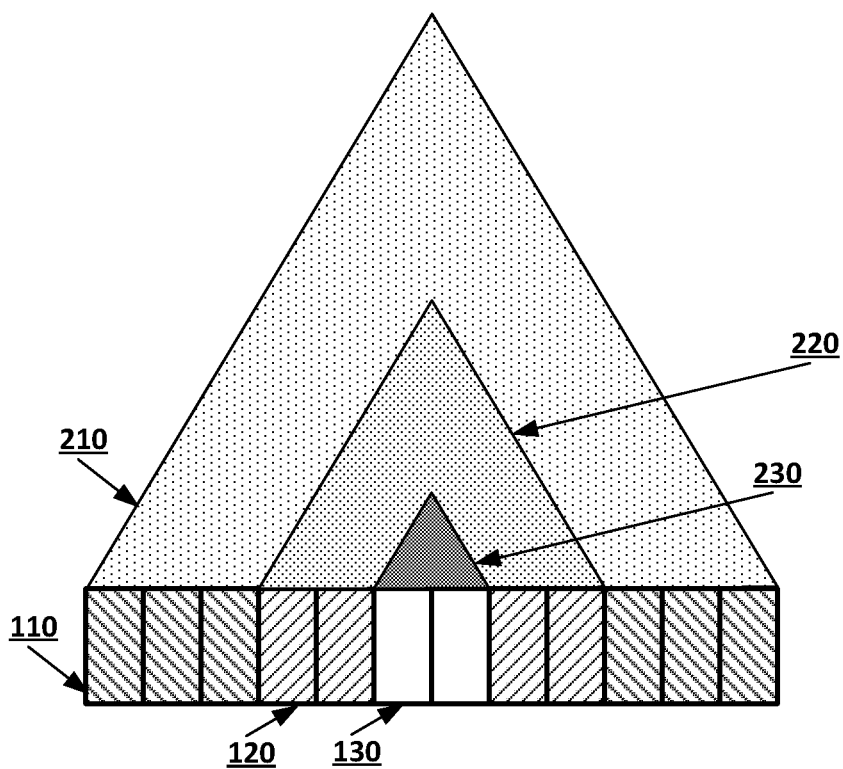

FIG. 2 shows an example ultrasonic transducer array according to an implementation of the disclosed subject matter. The ultrasonic transducer modules 110 that include low frequency ultrasonic transducers may generate low frequency ultrasonic waves 210. The ultrasonic transducer modules 120 that include medium frequency ultrasonic transducers may generate medium frequency ultrasonic wave 220. The ultrasonic transducer modules 130 that include high frequency ultrasonic transducers may generate high frequency ultrasonic waves 230.

Figure 3:
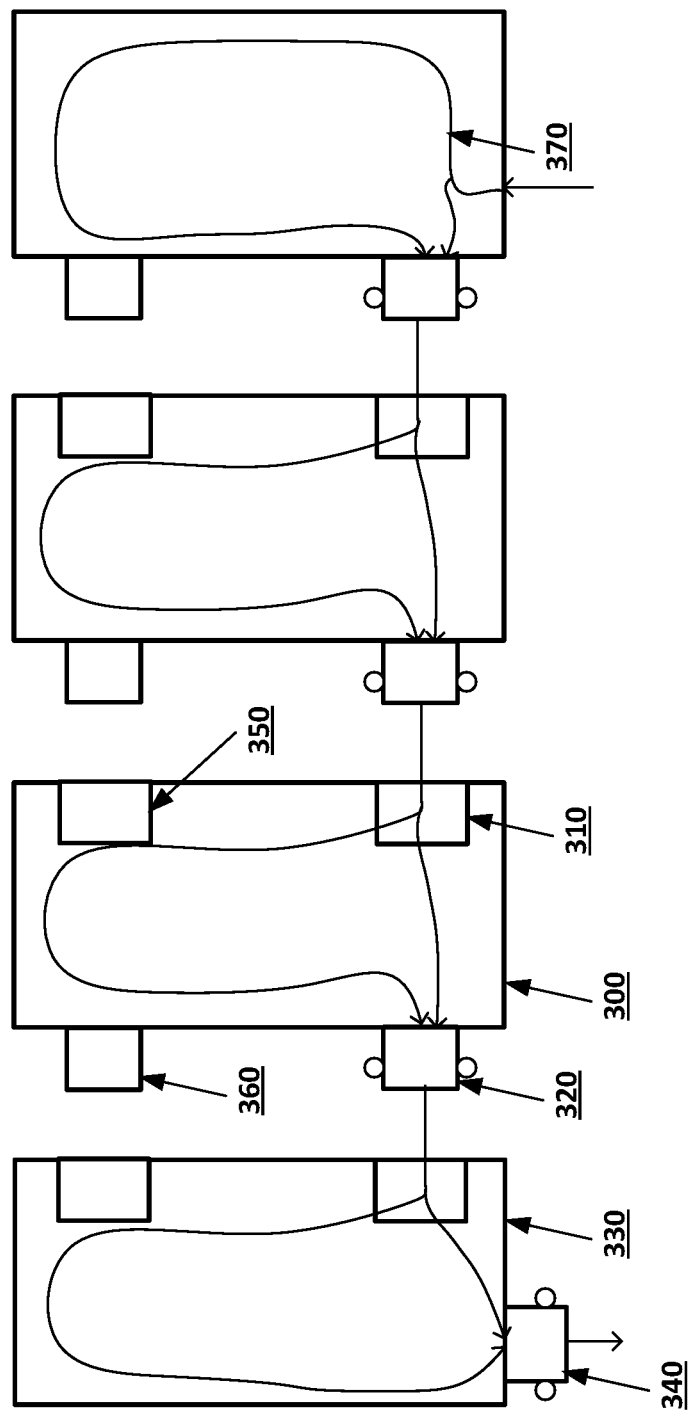

FIG. 3 shows example ultrasonic transducer modules according to an implementation of the disclosed subject matter. An ultrasonic transducer module 300 may include a common interface, which may include an intake port 310 and an exit port 320 for the intake and exit of a cooling fluid 370, such as water, to and from the ultrasonic transducer module 300. The intake port 310 may connect to the exit port of another ultrasonic transducer module, allowing for the flow of the cooling fluid 370 from one ultrasonic transducer module to another in a daisy-chain pattern. The ultrasonic transducer module 300 may also include connections 350 and 360, which may be used to physically connect the ultrasonic transducer module 300 to other ultrasonic transducer modules, and may also provide the electrical or optical connection of the common interface through which drive and receive signals from an ultrasonic controller system may be distributed to control the ultrasonic transducer element of the ultrasonic transducer modules. The ultrasonic transducer module 330 may be at the end of the daisy chain of ultrasonic transducer modules, and may include an exit port 340 that may connect to the frame of the ultrasonic transducer array.

Figure 4:
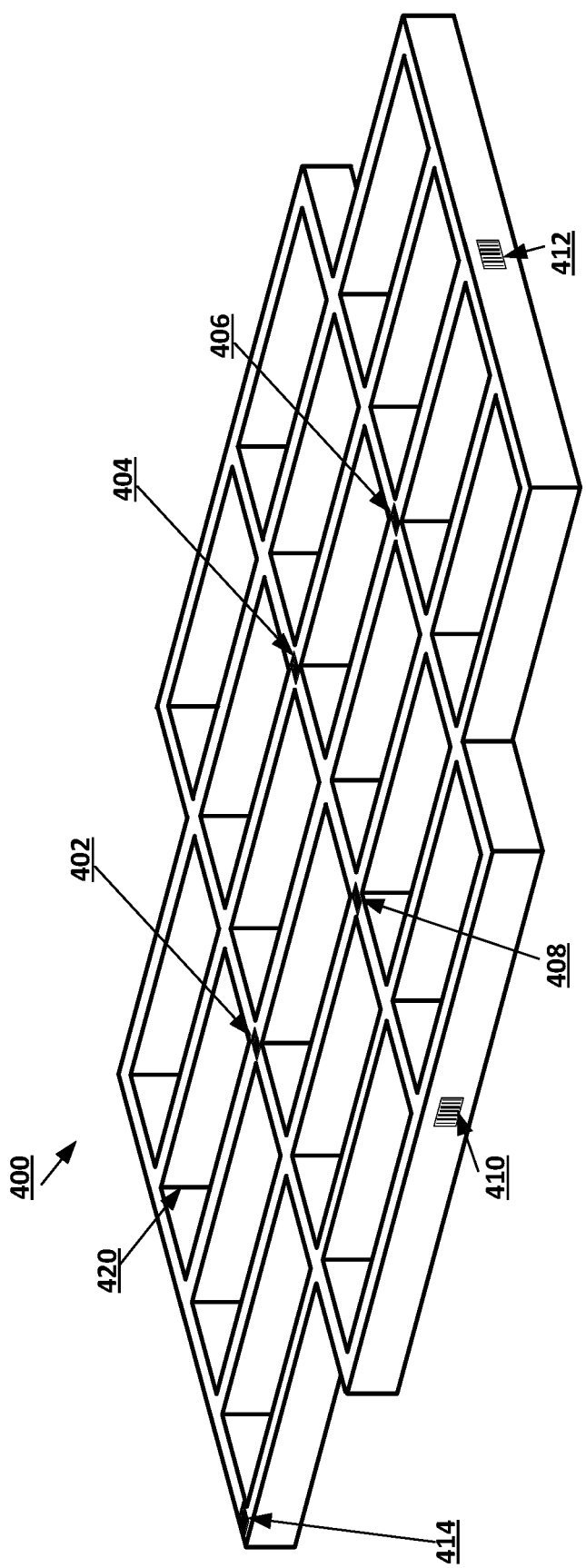

FIG. 4 shows an example ultrasonic transducer array frame according to an implementation of the disclosed subject matter. A modular ultrasonic transducer array frame 400 may define the physical position of the ultrasonic transducer modules in space to create an ultrasonic transducer array. The modular ultrasonic transducer array frame 400 may, for example, include a number of slots, such a slot 420, that may be constructed to accept the insertion of an ultrasonic transducer module, such as the ultrasonic transducer module 300. The arrangement of the slots in the modular ultrasonic transducer array frame 400 may define the physical positions of the ultrasonic transducer modules, such as the ultrasonic transducer module 300.

The modular ultrasonic transducer array frame 400 may be customized based on the intended use of the ultrasonic transducer array created using the frame. The modular ultrasonic transducer array frame 400 may allow for ultrasonic transducer arrays of various sizes, three-dimensional shapes, and orientations. The ultrasonic transducers of the ultrasonic transducer modules, such as the ultrasonic transducer module 300, used with the modular ultrasonic transducer frame 400 may be optimized for different frequency output, steering/directivity, and/or power output. Ultrasonic transducers with different ultrasonic transducer types may be mixed in the same modular ultrasonic transducer array frame 400, for example, with ultrasonic modules having different ultrasonic transducer types being inserted into different slots of the modular ultrasonic transducer array frame 400, creating a blended ultrasonic transducer array that may be optimized for a particular function or use. For example, an ultrasonic transducer array may be optimized for shear wave imaging or ablative therapy with integrated imaging for guidance and therapy progression tracking.

Ultrasonic transducer modules and modular ultrasonic transducer array frames, such as the modular ultrasonic transducer array frame 400, may be used to create large ultrasonic transducer arrays that may be invariant in resolution against depth. For example, the modular ultrasonic transducer array frame 400 may include a small array of ultrasonic transducer modules with high frequency transducers surrounded by an array of ultrasonic transducer modules with lower frequency transducers for achieving penetration, and which may be surrounded in turn by a larger array of ultrasonic transducer modules with lower frequency transducers to allow the ultrasonic transducer array to achieve an appropriate maximum penetration depth. The ultrasonic transducer modules in the ultrasonic transducer array may be of different sizes and shapes, and may be arranged in any suitable patterns. For example, ultrasonic transducer modules may be arranged in concentric rings or patterns approximating rings, which each ring including ultrasonic transducer modules with ultrasonic transducers of a specific type, or may be arranged in halves, quadrants, checkerboard patterns, or any other suitable pattern. Increasing the active area of the ultrasonic transducer array while maintaining all other parameter may improve the resolution of the ultrasonic transducer array. The number of ultrasonic transducer modules with ultrasonic transducers for each frequency array may increase to maintain the effective spatial resolution at target depth. Individual ultrasonic transducer modules may include more than one ultrasonic transducer.

The modular ultrasonic transducer array frame 400 may include fiducials, such as, for example, fiducials 402, 404, 406, 408, 410, 412, and 414. The fiducials 402, 404, 406, 408, 410, 412, and 414 may be, for example, bar codes or a two-dimensional patterns, such as a QR code, and all may be unique on the modular ultrasonic transducer array 400. For example, the fiducial 414 on the modular ultrasonic transducer array 400 frame may mark the location of the ultrasonic transducer module that serves as the zero module. The zero module may be the ultrasonic transducer module that is considered to be located at [0,0] in the array of ultrasonic transducer modules of the modular ultrasonic transducer array 400. Additional fiducials may be added to a frame to allow for more accurate determination of the orientation of the frame. For example, the fiducials 402, 404, 406, 408, 410, and 412 may all be used to mark specific sections of the modular ultrasonic transducer array 400 to allow for the determination of the location and orientation of the modular ultrasonic transducer array 400. The fiducials 402, 404, 406, and 408 may, for example, mark sections of the front of the modular ultrasonic transducer array 400, and may allow for the rotation of the modular ultrasonic transducer array 400 to be determined relative to, for example, a camera or scanner that is pointed at the front of the modular ultrasonic transducer array 400. The fiducials 410 and 412 may mark sections of the sides of the modular ultrasonic transducer array 400, and may be used by a camera or scanner to further determine the orientation of the modular ultrasonic transducer array 400 relative to the camera or scanner.

Figure 5:
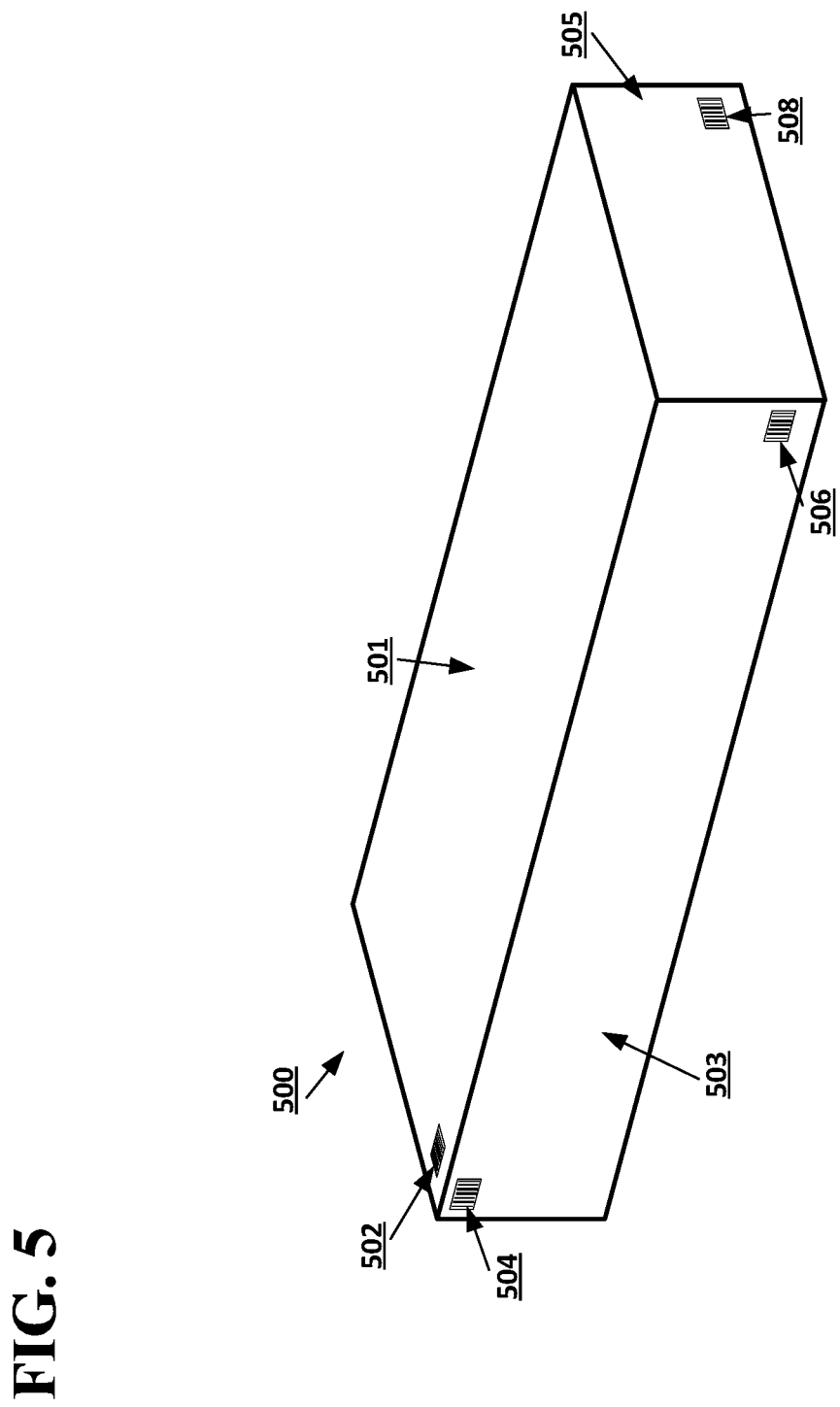

FIG. 5 shows an example ultrasonic transducer module according to an implementation of the disclosed subject matter. An ultrasonic transducer module 500 may be a module that includes an array of ultrasonic transducers. The ultrasonic transducer module 500 may be designed to be fit in to a frame, such as the modular ultrasonic transducer array frame 400, for example, in the slot 300. The ultrasonic transducer module 500 may include any number of fiducials, which may be, for example, bar codes, QR codes, or other two-dimensional codes placed on sections of the ultrasonic transducer module 500 to allow for the ultrasonic transducer module 500 to be located and its orientation to be determined. For example, a fiducial 502 may mark the location of the Zero Element of the ultrasonic transducer module 500. The Zero Element may be, for example, an ultrasonic transducer element that is considered to be located at the position [0,0] on the array of the ultrasonic transducers in the ultrasonic transducer module 500. Knowledge of the location of the Zero Element may be used by, for example, a ultrasonic controller system when generating signals to control the ultrasonic transducer elements of the ultrasonic transducer module 500. The fiducial 502 may appear on a top side 501 of the ultrasonic transducer module 500, which may be visible when the ultrasonic transducer module 500 is inserted into a frame such as the module ultrasonic transducer array frame 400. Fiducials 504 and 506 may mark the side of the ultrasonic transducer module 500, and fiducial 508 may mark a front end of the ultrasonic transducer module 500. The fiducials 504, 506, and 508 may all be visible when the ultrasonic transducer module 500 is inserted into a frame such as the modular ultrasonic transducer array frame 400. A ultrasonic controller system may be able to determine the orientation of the ultrasonic transducer module 500 based on locating any one of the fiducials 502, 504, 506, and 508, for example, using a camera or optical scanner.

Figure 6:
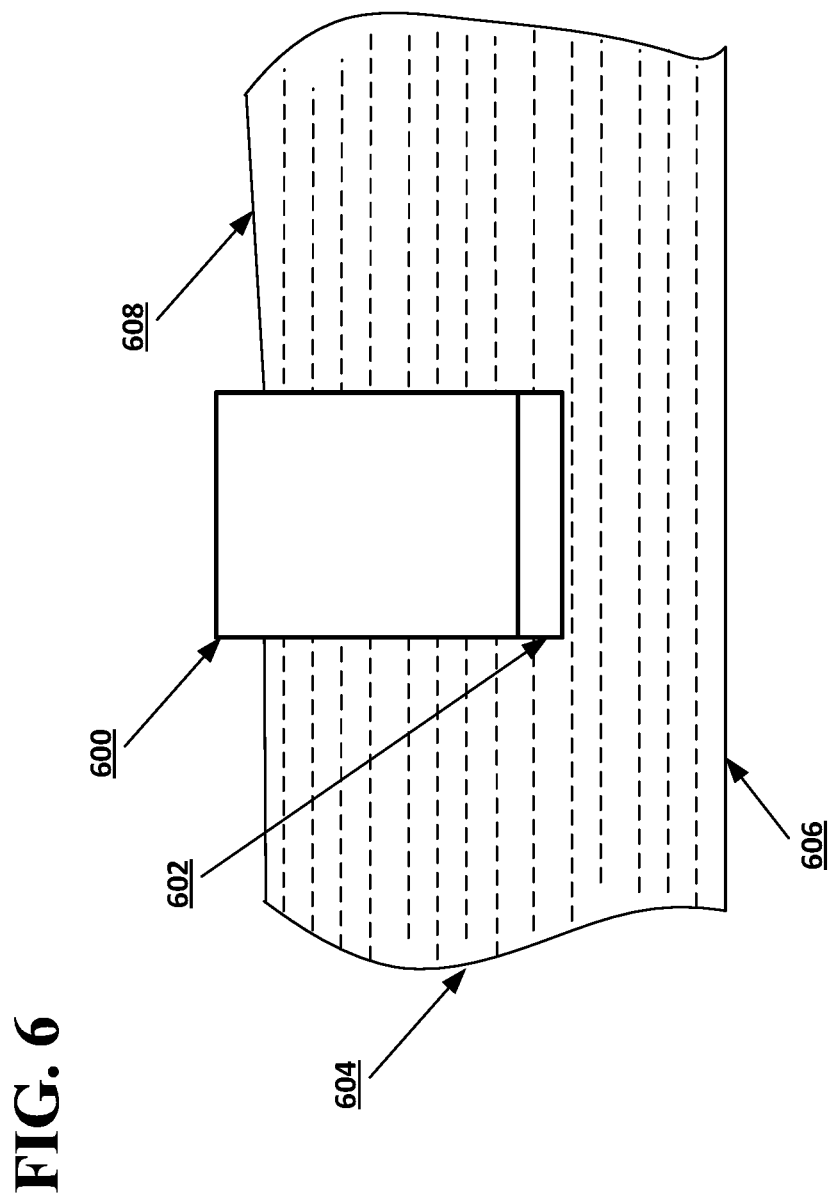

FIG. 6 shows an example ultrasonic transducer array and cooling fluid chamber according to an implementation of the disclosed subject matter. In some implementations, a cooling fluid chamber 604 may be used in front of or surrounding the front portion of an ultrasonic transducer array 600. The ultrasonic transducer array 600 may be constructed using, for example, the modular ultrasonic transducer array frame 400 and ultrasonic transducer modules such as, for example, the ultrasonic transducer modules 300 and 500. Ultrasonic transducers 602 may be located at the front of the ultrasonic transducer array 600, for example, being at the front of ultrasonic transducer modules. The cooling fluid chamber 604 may include a cooling fluid, such as, for example, water. The cooling fluid chamber 604 may have a membrane 606 across its front that may be in contact with the target of the ultrasonic waves and may pass ultrasonic energy to the target. The membrane 606 may be coated, for example, with planar graphite or diamond-like carbon (DLC), or any other suitable highly thermally conductive material which may allow for dispersal of surface hot spots. The coating may also act as an RF shield, which may improve the signal-to-noise ratio (SNR) of the ultrasonic transducer array 600 by keeping out unwanted RF energy. The frame of the ultrasonic transducer array 600, for example, the modular ultrasonic transducer array frame 400, may also be coated with a material similar to the material used to coat the membrane 600, allowing for similar reductions in RF interference. The depth of the cooling fluid chamber 604 may be adjustable, allowing for the gap between the target and front of the ultrasonic transducer array 600 to be tuned, which may disguise gaps between the ultrasonic transducer modules of the ultrasonic transducer array. This may allow better imaging with the ultrasonic transducer array 600 that uses ultrasonic transducer modules, such as the ultrasonic transducer modules 300 and 500, while also allowing the ultrasonic transducer array 600 to be positioned close to the surface target in situations where close coupling is desired. The cooling fluid chamber may be sealed around the ultrasonic transducer array 600 with a seal 608.

Figure 7:
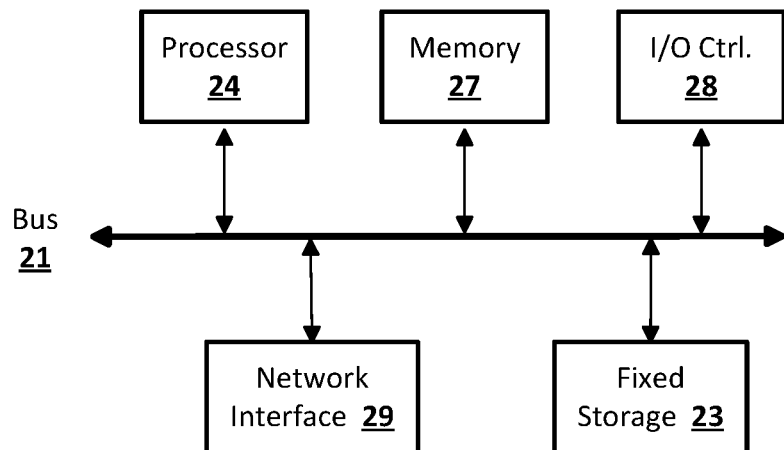

Embodiments of the presently disclosed subject matter may be implemented in and used with a variety of component and network architectures. FIG. 7 is an example computer system 20 suitable for implementing embodiments of the presently disclosed subject matter. The computer 20 includes a bus 21 which interconnects major components of the computer 20, such as one or more processors 24, memory 27 such as RAM, ROM, flash RAM, or the like, an input/output controller 28, and fixed storage 23 such as a hard drive, flash storage, SAN device, or the like. It will be understood that other components may or may not be included, such as a user display such as a display screen via a display adapter, user input interfaces such as controllers and associated user input devices such as a keyboard, mouse, touchscreen, or the like, and other components known in the art to use in or in conjunction with general-purpose computing systems.

The bus 21 allows data communication between the central processor 24 and the memory 27. The RAM is generally the main memory into which the operating system and application programs are loaded. The ROM or flash memory can contain, among other code, the Basic Input-Output system (BIOS) which controls basic hardware operation such as the interaction with peripheral components. Applications resident with the computer 20 are generally stored on and accessed via a computer readable medium, such as the fixed storage 23 and/or the memory 27, an optical drive, external storage mechanism, or the like.

Each component shown may be integral with the computer 20 or may be separate and accessed through other interfaces. Other interfaces, such as a network interface 29, may provide a connection to remote systems and devices via a telephone link, wired or wireless local- or wide-area network connection, proprietary network connections, or the like. For example, the network interface 29 may allow the computer to communicate with other computers via one or more local, wide-area, or other networks, as shown in FIG. 8.

Many other devices or components (not shown) may be connected in a similar manner, such as document scanners, digital cameras, auxiliary, supplemental, or backup systems, or the like. Conversely, all of the components shown in FIG. 7 need not be present to practice the present disclosure. The components can be interconnected in different ways from that shown. The operation of a computer such as that shown in FIG. 7 is readily known in the art and is not discussed in detail in this application. Code to implement the present disclosure can be stored in computer-readable storage media such as one or more of the memory 27, fixed storage 23, remote storage locations, or any other storage mechanism known in the art.

Figure 8:
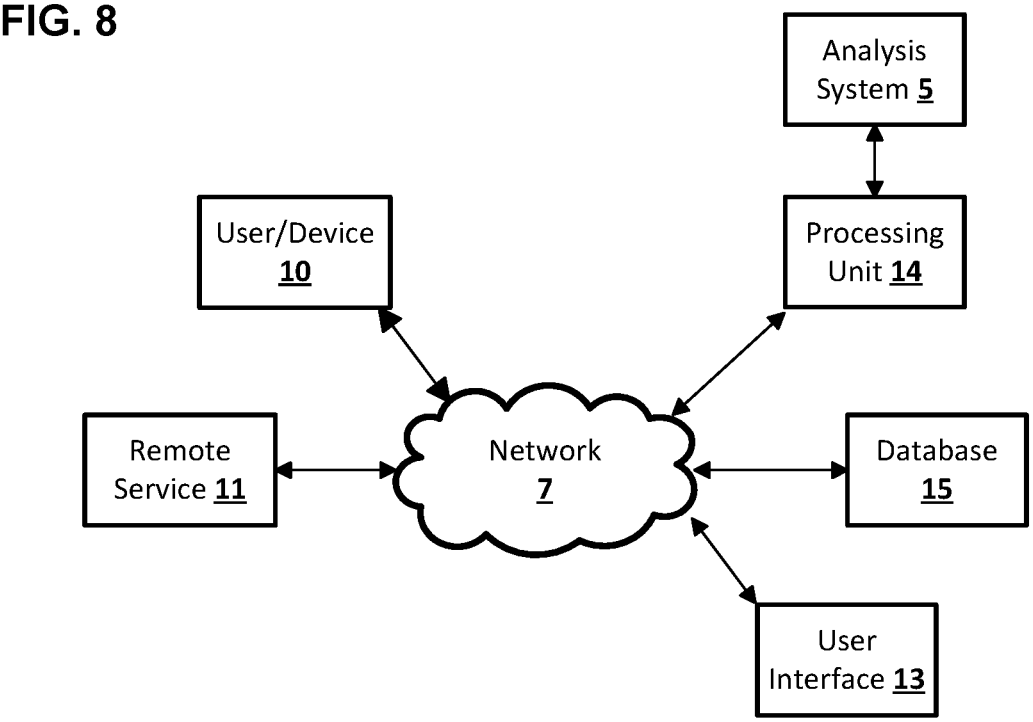

FIG. 8 shows an example arrangement according to an embodiment of the disclosed subject matter. One or more clients 10, 11, such as local computers, smart phones, tablet computing devices, remote services, and the like may connect to other devices via one or more networks 7. The network may be a local network, wide-area network, the Internet, or any other suitable communication network or networks, and may be implemented on any suitable platform including wired and/or wireless networks. The clients 10, 11 may communicate with one or more computer systems, such as processing units 14, databases 15, and user interface systems 13. In some cases, clients 10, 11 may communicate with a user interface system 13, which may provide access to one or more other systems such as a database table 15, a processing unit 14, or the like. For example, the user interface 13 may be a user-accessible web page that provides data from one or more other computer systems. The user interface 13 may provide different interfaces to different clients, such as where a human-readable web page is provided to web browser clients 10, and a computer-readable API or other interface is provided to remote service clients 11. The user interface 13, database table 15, and processing units 14 may be part of an integral system, or may include multiple computer systems communicating via a private network, the Internet, or any other suitable network. Processing units 14 may be, for example, part of a distributed system such as a cloud-based computing system, search engine, content delivery system, or the like, which may also include or communicate with a database table 15 and/or user interface 13. In some arrangements, an analysis system 5 may provide back-end processing, such as where stored or acquired data is pre-processed by the analysis system 5 before delivery to the processing unit 14, database table 15, and/or user interface 13. For example, a machine learning system 5 may provide various prediction models, data analysis, or the like to one or more other systems 13, 14, 15.

The foregoing description, for purpose of explanation, has been described with reference to specific embodiments. However, the illustrative discussions above are not intended to be exhaustive or to limit embodiments of the disclosed subject matter to the precise forms disclosed. Many modifications and variations are possible in view of the above teachings. The embodiments were chosen and described in order to explain the principles of embodiments of the disclosed subject matter and their practical applications, to thereby enable others skilled in the art to utilize those embodiments as well as various embodiments with various modifications as may be suited to the particular use contemplated.

The foregoing description, for purpose of explanation, has been described with reference to specific embodiments. However, the illustrative discussions above are not intended to be exhaustive or to limit embodiments of the disclosed subject matter to the precise forms disclosed. Many modifications and variations are possible in view of the above teachings. The embodiments were chosen and described in order to explain the principles of embodiments of the disclosed subject matter and their practical applications, to thereby enable others skilled in the art to utilize those embodiments as well as various embodiments with various modifications as may be suited to the particular use contemplated.

The invention claimed is:

1. An ultrasonic transducer module comprising:
   an ultrasonic transducer array comprising one or more ultrasonic transducer elements; each of the one or more ultrasonic transducer elements comprising electronics that control operation of the one or more ultrasonic transducer elements; and
   a common interface of the ultrasonic transducer module connected to the electronics that control operation of the one or more ultrasonic transducer elements, wherein the common interface provides signals from outside the ultrasonic transducer module to the electronics that control operation of the one or more ultrasonic transducer elements and provides signals from the electronics that control operation of the one or more ultrasonic transducer elements to outside the ultrasonic transducer module, and
   wherein the ultrasonic transducer module is configured to be attached to a modular ultrasonic transducer array frame,
   wherein the modular ultrasonic transducer array frame further comprises a backplane, and
   wherein the ultrasonic transducer module is connected to the backplane at a connection point of the common interface.

2. The ultrasonic transducer module of claim 1, further comprising a first connection point for the common interface and a second connection point for the common interface, wherein the first connection point accommodates connection to a second ultrasonic transducer module and the second connection point accommodates connection to a third ultrasonic transducer module.

3. The ultrasonic transducer module of claim 2, wherein the first connection point comprises an intake port and the second connection point comprises an exit port for a circulation of fluid through the ultrasonic transducer module.

4. The ultrasonic transducer module of claim 1, wherein the signals are electrical signals or optical signals.

5. The ultrasonic transducer module of claim 1, wherein the signals from outside the ultrasonic transducer module comprise control signals for the one or more ultrasonic transducer elements of the ultrasonic transducer array and wherein the signals from the electronics that control the one or more ultrasonic transducer elements comprise receive signals from the one or more ultrasonic transducer elements.

6. The ultrasonic transducer module of claim 1, further comprising one or more fiducials on surfaces of the ultrasonic transducer module.

7. The ultrasonic transducer module of claim 6, wherein at least one of the one or more fiducials marks a location of a zero element of the ultrasonic transducer array.

8. An ultrasonic transducer array comprising:
   a modular ultrasonic transducer array frame comprising mechanisms for the attachment of ultrasonic transducer modules to the ultrasonic transducer array frame; and
   two or more ultrasonic transducer modules, each of the two or more ultrasonic transducer modules comprising an array of ultrasonic transducer elements within the ultrasonic transducer module, at least two of the two or more ultrasonic transducer modules comprising arrays of ultrasonic transducer elements wherein the ultrasonic transducer elements are different between the at least two of the two or more ultrasonic transducer modules, wherein each of the two or more ultrasonic transducer modules comprises one or more connection points of a common interface and wherein the modular ultrasonic transducer array frame further comprises a backplane, and wherein two of the two or more ultrasonic transducer modules are connected to the backplane at connection points of the common interfaces of the two of the two or more ultrasonic transducer modules.

9. The ultrasonic transducer array of claim 8, wherein the modular ultrasonic transducer array frame comprises one or more fiducials on surfaces of the modular ultrasonic transducer array frame.

10. The ultrasonic transducer array of claim 9, wherein at least one of the one or more fiducials marks a zero module of the two or more ultrasonic transducer modules.

11. The ultrasonic transducer array of claim 8, further comprising at least one additional ultrasonic transducer module comprising an array of ultrasonic transducer elements that are different from the ultrasonic transducer elements of the arrays of the at least two of the two or more ultrasonic transducer modules.

12. The ultrasonic transducer array of claim 8, further comprising an ultrasonic controller system comprising a computing device and a device for detecting fiducials, wherein the ultrasonic controller system generates control signals for the two or more ultrasonic transducer modules based on determining an orientation of the two or more ultrasonic transducer modules and the modular ultrasonic transducer array frame through detecting one or more of the fiducials using the device for detecting the fiducials.

13. The ultrasonic transducer array of claim 12, wherein the control signals are based on electrical propagation delay for signal paths for the arrays of ultrasonic transducer elements of the two or more ultrasonic transducer modules.

14. The ultrasonic transducer array of claim 8, further comprising a cooling fluid chamber, wherein the modular ultrasonic transducer array frame and the two or more ultrasonic transducer modules are inserted into the cooling fluid chamber.

15. The ultrasonic transducer array of claim 8, wherein the modular ultrasonic transducer array frame comprises a structure that defines physical positions of the two or more ultrasonic transducer modules attached to the modular ultrasonic transducer array frame.

16. The ultrasonic transducer array of claim 11, wherein the ultrasonic transducer elements of the array of the at least one additional ultrasonic transducer module operate at a lower frequency than the ultrasonic transducer elements of the array of one of the at least two of the two or more ultrasonic transducer modules, and wherein the ultrasonic transducer elements of the array of the one of the at least two of the two or more ultrasonic transducer modules operate at a lower frequency than the ultrasonic transducer elements of the array of another one of the at least two of the two or more ultrasonic transducer modules.

17. The ultrasonic transducer array of claim 8, wherein two of the two or more ultrasonic transducer modules are connected to each other at connection points of the common interfaces of the two of the two or more ultrasonic transducer modules.

18. The ultrasonic transducer array of claim 8, wherein each of the two or more ultrasonic transducer modules comprises a connection point that is an intake port and a connection point that is an exit port that accommodate the circulation of fluid through the two or more ultrasonic transducer modules.

* * * * *